US007896905B2

(12) United States Patent
Lee et al.

(10) Patent No.: US 7,896,905 B2
(45) Date of Patent: Mar. 1, 2011

(54) BONE FIXATION APPARATUS

(76) Inventors: David Lee, Hattiesburg, MS (US); Eric Graham, Ocean Springs, MS (US); James P. Payne, Jr., Ocean Springs, MS (US)

( * ) Notice: Subject to any disclaimer, the term of this patent is extended or adjusted under 35 U.S.C. 154(b) by 1423 days.

(21) Appl. No.: 11/350,972

(22) Filed: Feb. 8, 2006

(65) Prior Publication Data

US 2006/0195096 A1    Aug. 31, 2006

Related U.S. Application Data

(60) Provisional application No. 60/651,314, filed on Feb. 9, 2005.

(51) Int. Cl.
*A61B 17/58* (2006.01)
(52) U.S. Cl. .......................... 606/271; 606/268; 606/270
(58) Field of Classification Search .............. 606/54–60, 606/246, 250–279, 300–331; 403/21, 22
See application file for complete search history.

(56) References Cited

U.S. PATENT DOCUMENTS

| | | | |
|---|---|---|---|
| 3,648,691 A | 3/1972 | Lumb et al. | |
| 4,369,769 A | 1/1983 | Edwards | |
| 4,433,677 A | 2/1984 | Ulrich et al. | |
| 4,604,995 A | 8/1986 | Stephens et al. | |
| 4,611,581 A | 9/1986 | Steffee | |
| 4,653,481 A * | 3/1987 | Howland et al. | 606/261 |
| 4,662,365 A * | 5/1987 | Gotzen et al. | 606/59 |
| 4,773,402 A | 9/1988 | Asher | |
| 4,887,596 A | 12/1989 | Sherman | |
| 4,957,495 A * | 9/1990 | Kluger | 606/58 |
| 4,978,348 A * | 12/1990 | Ilizarov | 606/57 |
| 4,987,892 A * | 1/1991 | Krag et al. | 606/264 |
| 5,047,029 A * | 9/1991 | Aebi et al. | 606/264 |
| 5,053,034 A * | 10/1991 | Olerud | 606/246 |
| 5,127,912 A * | 7/1992 | Ray et al. | 606/250 |
| 5,167,661 A * | 12/1992 | Wagenknecht | 606/54 |
| 5,254,118 A * | 10/1993 | Mirkovic | 606/264 |
| 5,261,907 A * | 11/1993 | Vignaud et al. | 606/60 |
| 5,261,909 A * | 11/1993 | Sutterlin et al. | 606/264 |
| 5,306,275 A * | 4/1994 | Bryan | 606/914 |
| 5,342,361 A * | 8/1994 | Yuan et al. | 606/59 |
| 5,380,323 A * | 1/1995 | Howland | 606/278 |
| 5,403,316 A * | 4/1995 | Ashman | 606/250 |
| 5,413,576 A * | 5/1995 | Rivard | 606/250 |
| 5,437,670 A * | 8/1995 | Sherman et al. | 606/278 |
| 5,474,551 A * | 12/1995 | Finn et al. | 606/264 |
| 5,545,167 A * | 8/1996 | Lin | 606/278 |

(Continued)

*Primary Examiner* — Eduardo C Robert
*Assistant Examiner* — Mary Hoffman
(74) *Attorney, Agent, or Firm* — Garvey, Smith, Nehrbass & North, L.L.C.; Brett A. North

(57) ABSTRACT

What is provided is a fixation system that offers a strong and stable construct for maximum fusion augmentation and yet is versatile enough for any patient and is easy to use. Disclosed is a connection assembly for connecting a spinal implant, the assembly comprising: a body, the body including a body opening for receiving at least a portion of a first connector; a swivel having first and second ends and being operatively connected to the body, the first end including a swivel opening for receiving at least a portion of a second connector; a locking plate having an arm at least partially extending into the body opening; a locking unit operatively connected to the body and contacting the second end of the swivel; and whereby activation of the locking unit causes the arm to engage the first connector and swivel opening to engage the second connector thereby preventing relative rotation between the first and second connectors.

11 Claims, 6 Drawing Sheets

U.S. PATENT DOCUMENTS

| | | | |
|---|---|---|---|
| 5,549,607 A * | 8/1996 | Olson et al. | 606/251 |
| 5,611,800 A * | 3/1997 | Davis et al. | 606/250 |
| 5,634,925 A | 6/1997 | Urbanski | |
| 5,643,262 A * | 7/1997 | Metz-Stavenhagen et al. | 606/261 |
| 5,662,651 A * | 9/1997 | Tornier et al. | 606/60 |
| 5,688,275 A * | 11/1997 | Koros et al. | 606/264 |
| 5,693,053 A * | 12/1997 | Estes | 606/250 |
| 5,716,355 A * | 2/1998 | Jackson et al. | 606/252 |
| 5,741,255 A * | 4/1998 | Krag et al. | 606/264 |
| 5,876,403 A * | 3/1999 | Shitoto | 606/308 |
| 5,885,285 A * | 3/1999 | Simonson | 606/278 |
| 5,976,133 A * | 11/1999 | Kraus et al. | 606/54 |
| 5,997,539 A * | 12/1999 | Errico et al. | 606/278 |
| 6,022,348 A * | 2/2000 | Spitzer | 606/54 |
| 6,063,089 A * | 5/2000 | Errico et al. | 606/278 |
| 6,110,173 A * | 8/2000 | Thomas, Jr. | 606/252 |
| 6,183,473 B1 * | 2/2001 | Ashman | 606/278 |
| 6,231,575 B1 | 5/2001 | Krag | |
| 6,248,107 B1 * | 6/2001 | Foley et al. | 606/264 |
| 6,309,390 B1 * | 10/2001 | Le Couedic et al. | 606/264 |
| 6,402,749 B1 * | 6/2002 | Ashman | 606/278 |
| 6,514,253 B1 * | 2/2003 | Yao | 606/53 |
| 6,520,962 B1 * | 2/2003 | Taylor et al. | 606/278 |
| 6,551,318 B1 * | 4/2003 | Stahurski | 606/252 |
| 6,579,292 B2 * | 6/2003 | Taylor | 606/278 |
| 6,626,904 B1 * | 9/2003 | Jammet et al. | 606/266 |
| 6,676,661 B1 * | 1/2004 | Benlloch et al. | 606/264 |
| 6,685,705 B1 * | 2/2004 | Taylor | 606/278 |
| 6,736,817 B2 * | 5/2004 | Troxell et al. | 606/252 |
| 6,832,999 B2 | 12/2004 | Ueyama et al. | |
| 6,958,066 B2 * | 10/2005 | Richelsoph et al. | 606/252 |
| RE39,035 E * | 3/2006 | Finn et al. | 606/264 |
| 7,314,467 B2 * | 1/2008 | Howland | 606/86 A |
| 7,473,269 B1 * | 1/2009 | Hynes | 606/279 |
| 7,485,132 B1 * | 2/2009 | McBride et al. | 606/250 |
| 7,575,587 B2 * | 8/2009 | Rezach et al. | 606/278 |
| 7,635,380 B2 * | 12/2009 | Zucherman et al. | 606/267 |
| 2002/0042614 A1 * | 4/2002 | Ueyama et al. | 606/61 |
| 2002/0173789 A1 * | 11/2002 | Howland | 606/61 |
| 2003/0105460 A1 * | 6/2003 | Crandall et al. | 606/61 |
| 2003/0176862 A1 * | 9/2003 | Taylor et al. | 606/61 |
| 2003/0176864 A1 * | 9/2003 | Ueyama et al. | 606/61 |
| 2004/0054371 A1 * | 3/2004 | Dierks et al. | 606/73 |
| 2004/0087949 A1 * | 5/2004 | Bono et al. | 606/61 |
| 2005/0090821 A1 * | 4/2005 | Berrevoets et al. | 606/61 |
| 2005/0113830 A1 * | 5/2005 | Rezach et al. | 606/60 |
| 2006/0004360 A1 * | 1/2006 | Kramer et al. | 606/61 |
| 2006/0025770 A1 * | 2/2006 | Schlapfer et al. | 606/61 |
| 2006/0149231 A1 * | 7/2006 | Bray | 606/61 |
| 2006/0167455 A1 * | 7/2006 | Clement et al. | 606/61 |
| 2006/0271051 A1 * | 11/2006 | Berrevoets et al. | 606/61 |
| 2007/0055239 A1 * | 3/2007 | Sweeney et al. | 606/61 |
| 2007/0123863 A1 * | 5/2007 | Winslow et al. | 606/61 |
| 2007/0173833 A1 * | 7/2007 | Butler et al. | 606/61 |
| 2009/0103998 A1 * | 4/2009 | Gagneur | 411/196 |
| 2009/0204155 A1 * | 8/2009 | Aschmann | 606/264 |
| 2010/0036417 A1 * | 2/2010 | James et al. | 606/246 |

* cited by examiner

BONE FIXATION APPARATUS

CROSS-REFERENCE TO RELATED APPLICATIONS

Priority of U.S. provisional patent application Ser. No. 60/651,314, filed Feb. 9, 2005, is hereby claimed. This application is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND

The present invention relates to surgical systems and more particularly relates to an improved bone or spinal fixation apparatus in the form of a strong and stable construct for maximum fusion augmentation with improved versatility and ease of use, and including an improved rotation and adjustment system.

There are a number of surgical procedures which require a fixation of portions of the spine with respect to one another. Typically, bone screws are employed in the fixation of the spine. The implantation of bone screws is a surgical procedure which involves the formation of one or more surgical openings in adjacent portions of the spine, with threaded bone screws being implanted into these surgical openings. Connective structure such as rods or plates extend between the various spine members by connecting the adjacent bone screws.

An early spinal fixation system can be seen in the Lumb et al. U.S. Pat. No. 3,648,691 entitled "Method of Applying Vertebral Appliance". In the Lumb patent, a method of applying a vertebral appliance for use in bridging one or more diseased or damaged vertebra uses a pair of elongated flexible multiple apertured plates having fasteners which are used to clamp the plate to opposite sides of the spinous processes being spanned. Each strap or plate is of a length adapted to span at least two spinous processes and project there beyond each end so that the fasteners can be passed both behind and in front thereof as well as through the interspinous gap there between. The apertures are located considerably closer together than adjacent processes and they are fastened to the latter in position such that at least one opening registers with each one to receive a growth or soft bony tissue that eventually extrudes therein.

The Edwards U.S. Pat. No. 4,369,769 shows a spinal fixation system using elongated rods used to bridge across various portions of the spine. In the Edwards '769 patent a spinal fixation device is provided in which sleeves or spacers are placed over and around spinal rods in order to obtain a better reduction of spinal fractures or spinal deformities. These sleeves can be made in various thicknesses so that the surgeon can obtain optimum fixation in each case. The sleeves are made of any biologically compatible material.

Use of bone screws and connecting rods is also seen in the Ulrich et al. U.S. Pat. No. 4,433,677 entitled "Implantable Splint for Correction Lumbosacral Spondylodesis". In the Ulrich patent a spinal distraction splint has two like anchor screws extending along respective longitudinal screw axes and adapted to be anchored in the pelvis with the axes crossing. Each of the screws has a head formed with a transverse open recess centered on respective transverse axis and with an angular array of teeth centered on and angularly spaced about the respective transverse axis.

Another patent that shows screws as part of a spinal stabilizer is the Stephens et al. U.S. Pat. No. 4,604,995. In the Stephens patent a surgical implant is used for imparting stability to the thoraco-lumbar spine by fixation of the implant to the spine with segmental spinal instrumentation. The implant comprises a unitary rod having a generally rectangular configuration formed by a pair of spaced apart branches, mirror image duplicated of one another and equally spaced apart along their length.

The Steffee U.S. Pat. No. 4,611,581 entitled "Apparatus for Straightening Spinal Columns" provides an apparatus to reduce the extent of displacement between adjacent vertebra in a person's spinal column and to subsequently maintain the vertebra in a reduced displacement relationship. When the apparatus is to be installed, holes are formed in the displaced vertebra and in vertebra on opposite sides of the displaced vertebra. Force transmitting members are mounted in the holes in the vertebra. A spinal plate is then positioned on the spinal column with the force transmitting members extending outwardly through the slots in the spinal plate. Nuts are tightened on the force transmitting members connected with vertebra on opposite sides of the displaced vertebra to anchor the spinal plate in place. A nut on the force transmitting member connected with the displaced vertebra is then tightened to pull the displaced vertebra to a desired position. In one embodiment, the force transmitting member has a relatively large diameter helix which engages a side wall of the hole in the displaced vertebra. In another embodiment, an insert is positioned in a hole in the displaced vertebra and expanded by the force transmitting member to securely grip the vertebra.

A device which uses clamps as opposed to bone screws is the Asher U.S. Pat. No. 4,773,402 entitled "Dorsal Transacral Surgical Implant" wherein a pair of spine engageable rods, contoured to the desired spinal column configuration are provided with a yoke and foot element being attached to the pair of rods during use.

The Sherman U.S. Pat. No. 4,887,596 shows a pedicle screw for use in internal fixation of the spine comprising a shaft threaded at one end for insertion into a bone and at the other end having a yoke for receiving a rod, the yoke having a cusp adapted to bear against the rod and clamps for holding the rod against the cusp while permitting adjustment of the angle between the rod and the yoke.

Each of the above referenced patents are incorporated herein by reference.

One of the problems with the application of a spinal fixation system is the limited adjustability of the connective structures with respect to a plurality of spaced apart bone screws which had been placed in the spine at various angles.

Another problem with the application of a spinal fixation system is the ease with which the surgeon will install the clamping systems.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

BRIEF SUMMARY

The apparatus of the present invention solves the problems confronted in the art in a simple and straightforward manner.

What is provided is a fixation system that offers a strong and stable construct for maximum fusion augmentation and yet is versatile enough for any patient and is easy to use.

In one embodiment is provided an improved spinal fixation apparatus having improved fit through relative adjustments between the screws and rods.

The drawings constitute a part of this specification and include exemplary embodiments to the invention, which may be embodied in various forms.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

Figure 3:
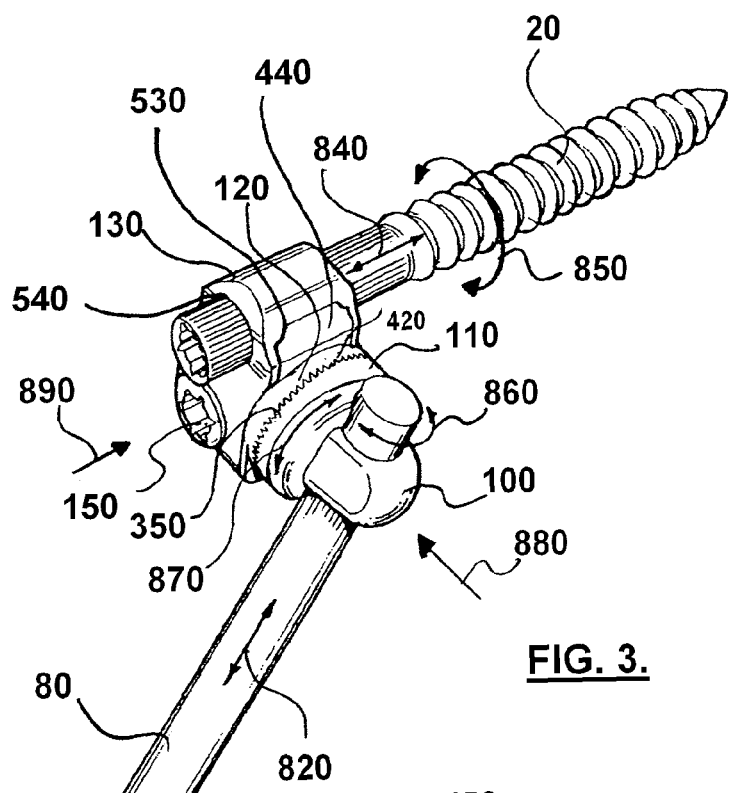
FIG. 3 is a perspective view of the clamp of FIG. 1 showing arrows schematically indicating various adjustments which can be made.
Figure 4:
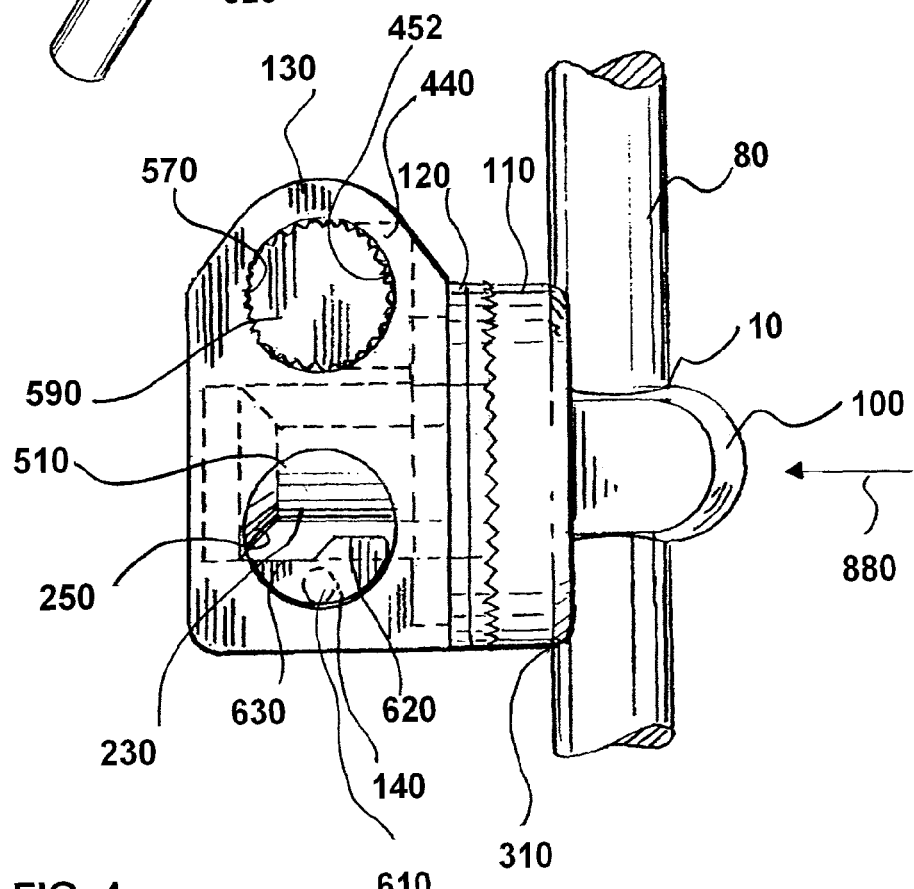
FIG. 4 is a top view of the clamp of FIG. 1 with set screw removed.
Figure 5:
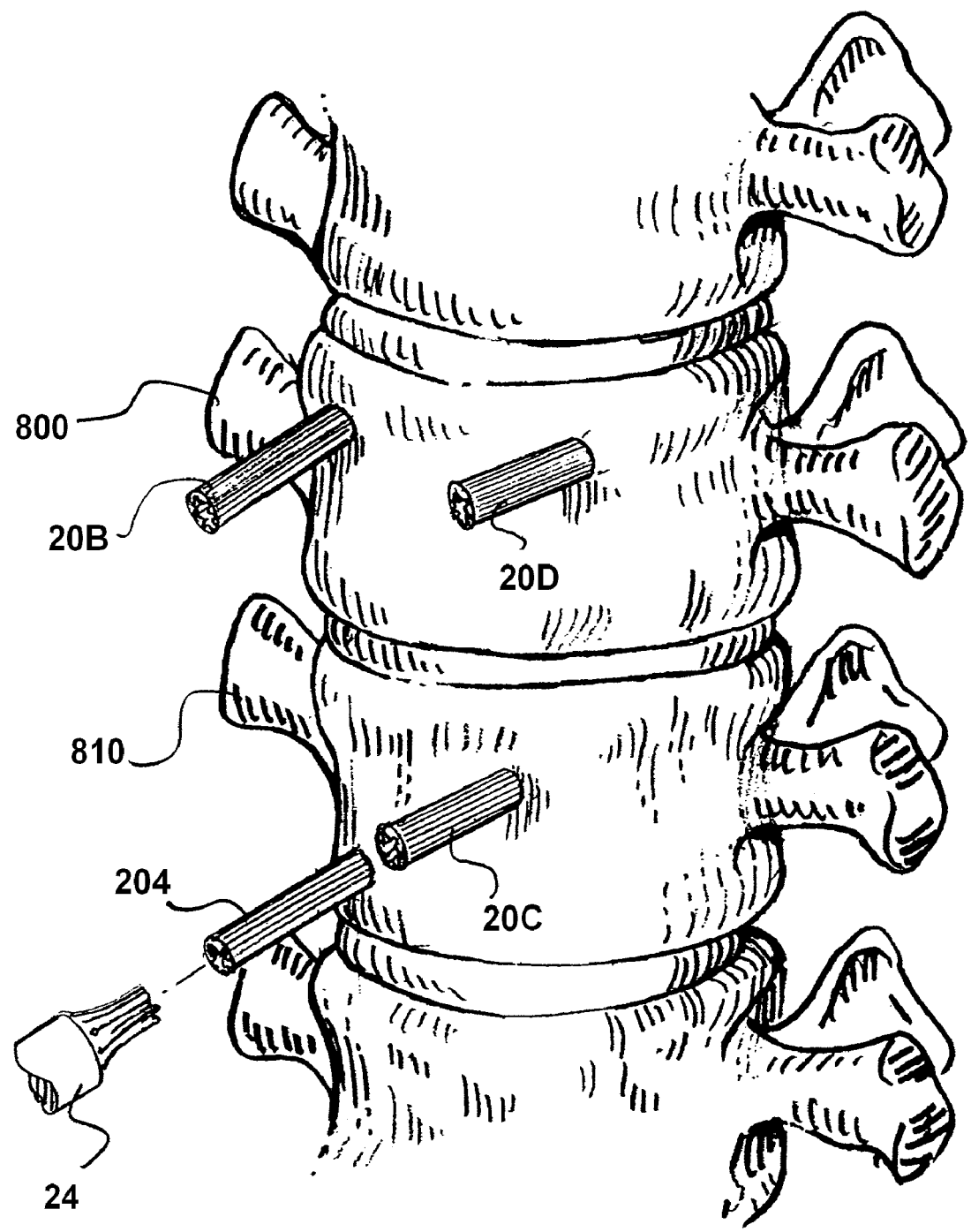
FIG. 5 is a perspective view of a two vertebrae to be fused using the clamp of FIG. 1A and shown a plurality of screws installed in the vertebrae (shown from the rear of a person's body)
Figure 6:
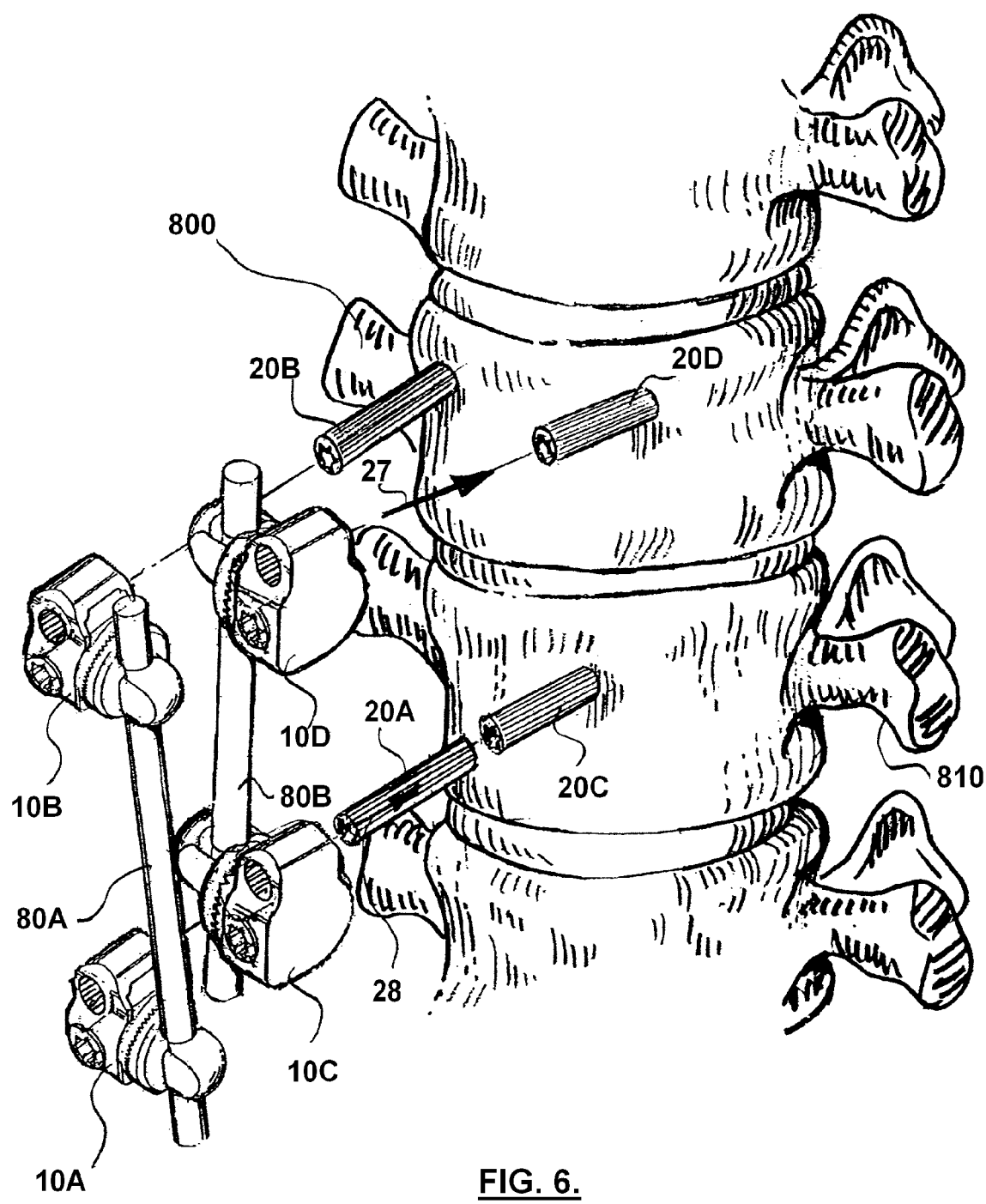
FIG. 6 is a perspective view of the two vertebrae of FIG. 5 where two sets of clamps are being placed on the plurality of screws (shown from the rear of a person's body)
Figure 7:
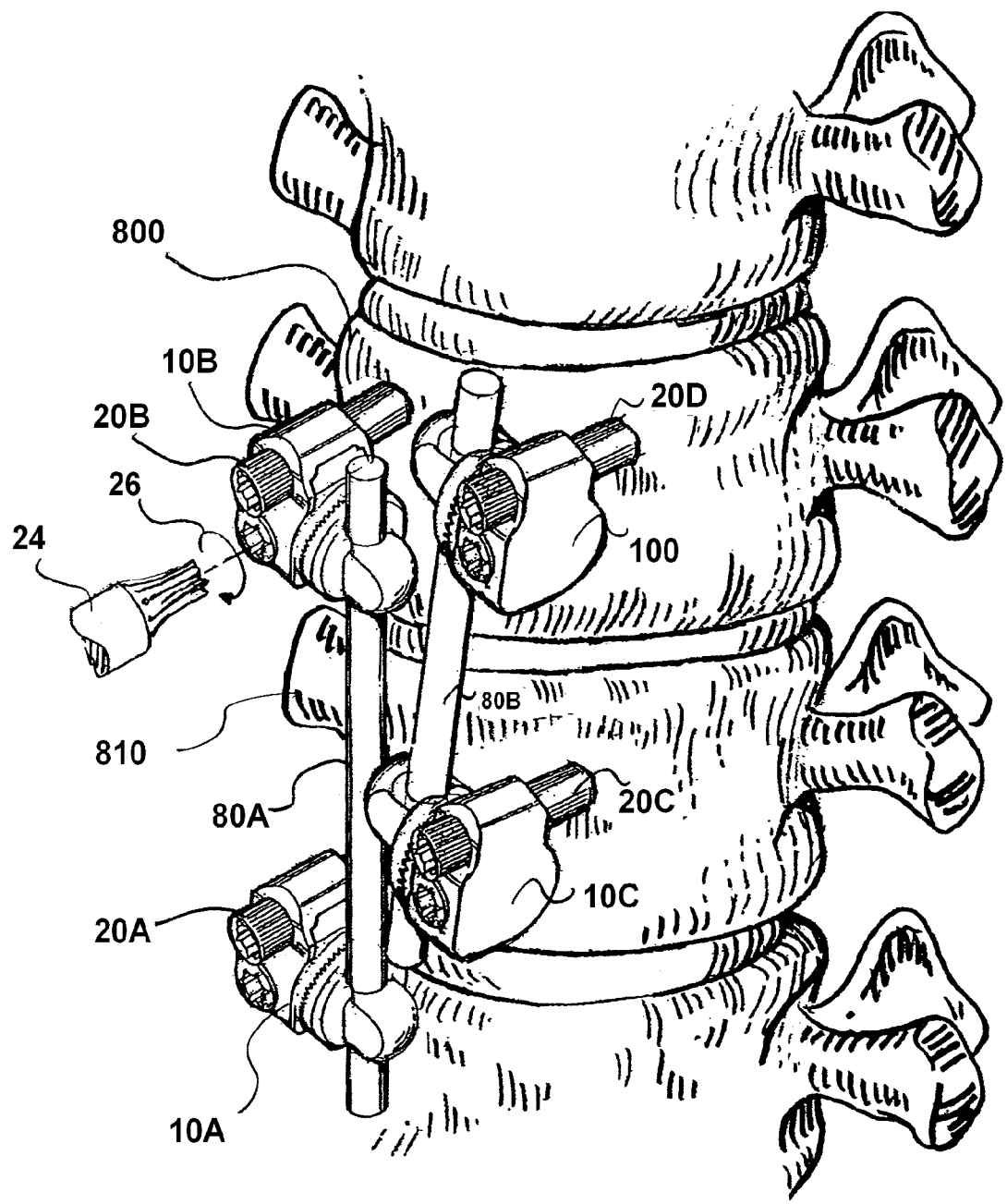
FIG. 7 shows the two vertebrae of FIGS. 5 and 6 with the clamps being locked in position (shown from the rear of a person's body).

FIGS. 5-7 illustrate the process of fusing two vertebrae 800, 810 using a plurality of clamps 10A, 10B, 10C, and 10D of the construction shown in FIGS. 1-4. All clamps 10 can be of substantially identical construction (however, clamps 10A, 10B are shown as mirror images of clamps 10C, 10D to have both rods 80A, 80B set between the clamps). The operation of clamp 10A will be described in specific detail. In each case, for an effective fusion, vertebra 800 is held in contact with vertebra 810. In its simplest form, clamp 10A can be mechanically connected to vertebra 810 and a second clamp 10B can be mechanically connected to vertebra 800. This mechanical connection can be achieved by means of screws 20 or other fasteners which are compatible with vertebrae and the human body and installed by a driver 24. Clamp 10A and 10B can be mechanically connected to each other by rod 80A. On the opposite side of vertebrae 800,810 a second set of clamps 10C,10D and rod 80B can be used to mechanically connect vertebrae 800,810. These two clamps can be placed over screws 20C, 20D as schematically indicated by arrows 28, 27. A driver 24 can be used to mechanically lock each clamp through tightening of the clamp's set screw by turning in the direction of arrow 26. The two rods 80A,80B can be mechanically connected to each other for additional support. Over a period of time, after being mechanically connected, the bone in vertebrae 800,810 will grow or fuse together thus completing the fusion.

Figures 1, 1A:
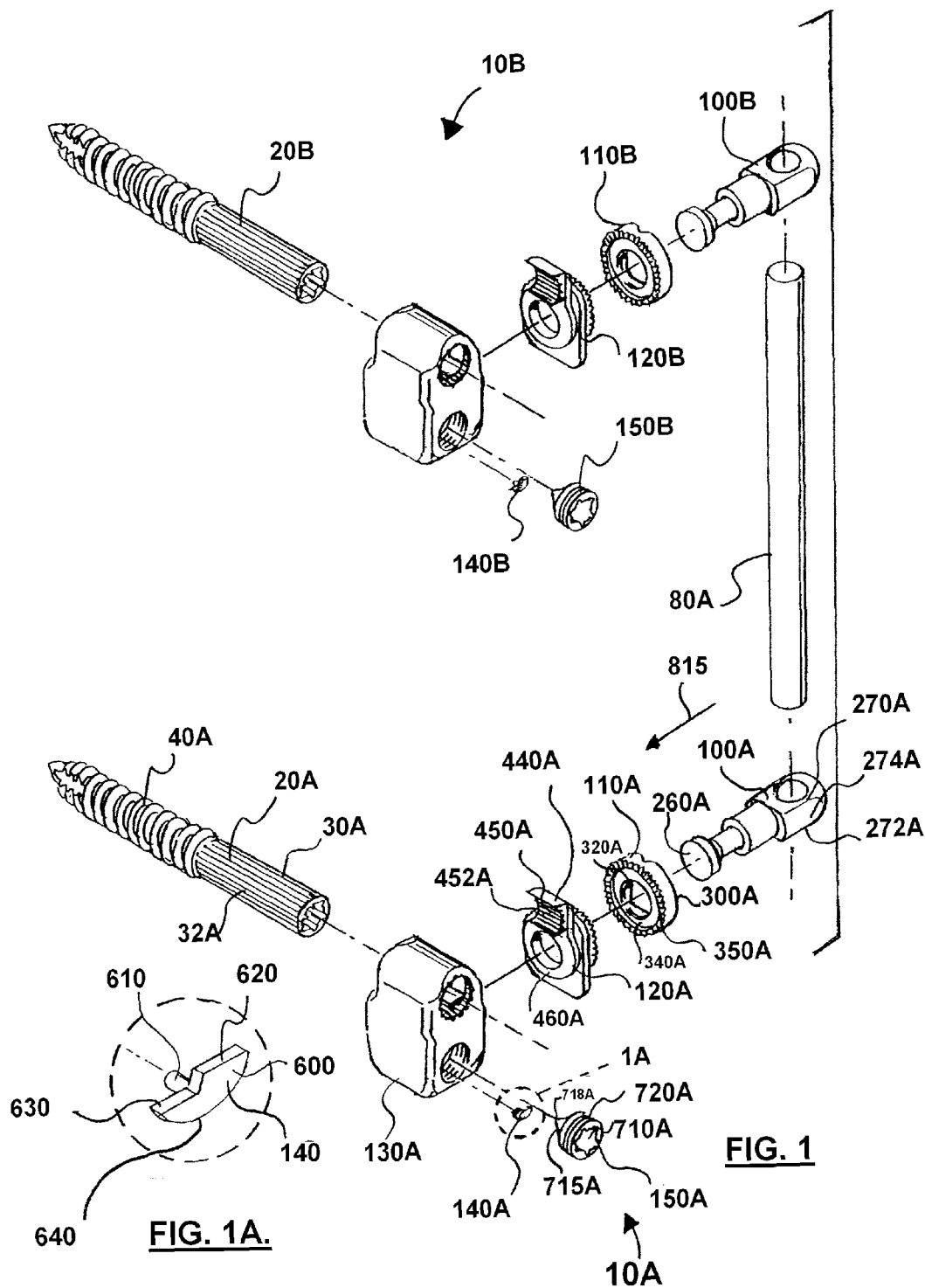
FIG. 1 is an exploded perspective view of one embodiment of a preferred clamp.
FIG. 1A is an enlarged perspective view of a retainer.
Figure 2:
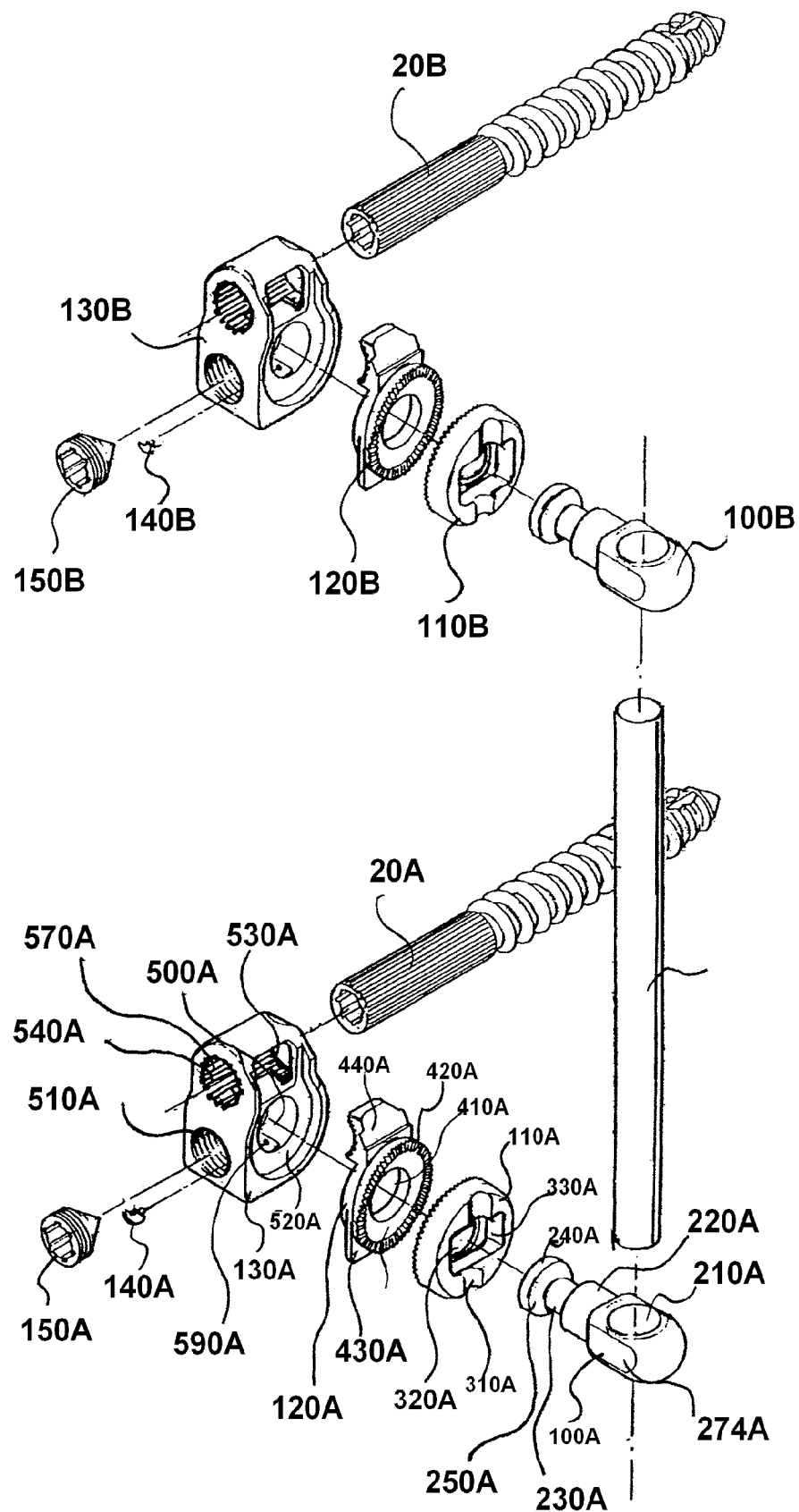
FIG. 2 is an exploded perspective view of the clamp of FIG. 1, but taken from the opposite side as that shown in FIG. 1.

FIGS. 1 and 2 are exploded views of a preferred clamp 10 (showing two examples of the clamp 10A, 10B). Although constructed similar to each other the individual components of clamp 10A and clamp 10B will be differentiated by the addition of an "A" or a "B." Clamp 10 can be used to mechanically connect bone screws 20 with rods 80. Clamp 10 can comprise body 130, locking plate 120, rod disc 110, and swivel 100. Set screw 150 and retainer 140 can be used to lock in place swivel 100, rod clamp 110, and locking plate 120 (which can be assembled in the direction of arrow 815 as shown in FIG. 1). Alternatively, set screw 150 can be used by itself without retainer 140. Screw 20 can be connected to body 130 through bore 540. Rod 80 can be connected to body 130 through opening 210. The mechanics of the connections with rod 80 and screw 20 will be described below.

During installation each clamp 10 preferably is adjustable in various directions with respect to rod 80 and screw 20 (as schematically indicated by FIG. 3). FIG. 3 shows clamp 10 having screw 20 and rod 80 mounted. Because of variations when inserting screw 20 in a specific vertebra, clamp 10 is provided with various adjustment options related to screw 10. For screw 20 the two principal adjustment options are indicated by arrows 840,850. The longitudinal axis of screw 20 is shown parallel to arrow 840. Rod 80 is shown being parallel to arrow 820. When clamp 10 is not tightened body 130 can slide relative to screw 20 in both directions indicated by arrow 840. Also when clamp 10 is not locked, body 130 can rotate relative to screw 20 in both directions indicated by arrow 850.

For rod 80 the three principal adjustment options are indicated be arrows 820,860,870. When clamp 10 is not locked, rod 80 can slide relative to body 130 in both directions indicated by arrow 820. Additionally, when not locked, rod 80 can rotate relative to body 130 in both directions indicated by arrow 870 and both directions indicated by arrow 860.

The above described possible relative movements between rod 80 and body 130 along with the relative movements between body 130 and screw 20 provide adjustability between rod 80 and screw 20. The relative movement between rod 80 and screw 20 facilitates fixation of two or more clamp 10 members regardless of the relative positions (angular, height, location) of respective screws 20. For example, as shown in FIGS. 5-7, clamps 10A,10B can be connected to rod 80A even where screws 20A,20B are not parallel to each other and are not at the same relative height.

FIG. 4 is a top view of a portion of clamp 10 showing rod 80 inserted into opening 210 of swivel 100 and swivel 100 inserted into rod disc 110. Rod 80 can sit in recess 310. FIG. 3 is a perspective view of clamp 10 showing bone screw 20 inserted into bore 540 of body 130 with locking plate 120 lying on top of body 130. FIGS. 3 and 4 illustrate how arm 440 of locking plate 120 enters opening 530 of body 130 to engage bone screw 20. Also shown is tapped bore 510 wherein set screw 150 enters to lock clamp 10.

Below the individual components of clamp 10 (including body 130, locking plate 120, rod disc 110, and swivel 100) will be described in specific detail.

Swivel 100 can comprise base 240, shaft 230, mid portion 220, and head 200. Base 240 can be circular and include beveled or angled edge 250 and bottom 260. Beveled or angled edge 250 can be used as the contact point of set screw 150 (when set screw 150 is tightened in the direction of arrow 890, swivel 100 is pulled in the direction of arrow 880 thereby locking clamp 10—see FIG. 3). The top of head 200 can have a rectangular cross section with rounded edges. Shaft 230 can include a circular cross section which is smaller than base 240. Mid portion 220 can include a circular cross section which is larger than shaft 230. Head 200 can include opening 210, face 270, and a plurality of edges 272,274.

Rod disc 110 can include top 300 and bottom 340. On bottom 340 can include a plurality of teeth 350. Recess 310 can be included on top 300. First bore 320 can pass from top 300 to bottom. Second bore 330 can be included which starts at the top but stops before hitting the bottom. First bore 320 can be circular. Second bore 330 is preferably a non-circular shape to restrict relative rotation between rod disc 110 and swivel 100 (head 200 of swivel 100 can seat in second bore 330). Second bore 300 can operatively connect with head 200 of swivel 100. Rod 80 can seat in recess 310 when at least partially inserted in opening 210. When clamp 10 is locked, rod 80 can be frictionally engaged between opening 210 and recess 310. Also when clamp 10 is locked, plurality of teeth 350 of rod disc 110 can be engaged with plurality of teeth 420 of locking plate 120 thereby preventing relative rotation between rod disc 110 and locking plate 120. In a preferred embodiment seventy two teeth are used, but the number can vary based on size and strength considerations. Using sixty teeth 420 provide positioning approximately every six degrees while seventy two teeth 420 provide positioning approximately every five degrees.

Locking plate 120 can include arm 440 and bore 410. Arm 440 can include cup 450 which includes plurality of ribs 452. Plurality of ribs 452 can be used to prevent relative rotation between bone screw 20 and arm 440 (and also body 130). When arm 440 of locking plate 120 enters opening 530 of body 130, relative rotation between locking plate 120 and body 130 is restricted.

Body 130 can include transverse bore 500 for insertion of base 240 of swivel 100. Longitudinal bore 540 can be included for receiving screw 20. Longitudinal bore 540 can include plurality of ribs 570. Plurality of ribs 452 can be used to prevent relative rotation between bone screw 20 and body 130. Plurality of ribs 452 can be placed on only a radial portion of longitudinal bore 540 (and not around the complete radius of bore 540). Recessed area 520 can be included to receive locking plate 120. Opening 530 can be included to receive arm 440 of locking plate 120. Body 130 can include threads 550 in tapped bore 510. At the base of tapped bore 510 can be included bore 590 and edge 560.

FIG. 1A shows an enlarged perspective view of retainer 140. Retainer 140 can include top 600, shaft 610, first edge 620, second edge 630, curved surface 640, and bottom 650. Shaft 610 can be inserted in bore 590 of body 130 (see FIGS. 1, 2, and 4). Retainer 140 can be used to provide support for set screw 150, when set screw 150 is contacting base 240 of swivel 100. Shaft 610 of retainer 140 can be press fit into bore 590 as a means for retaining swivel 100 in body 130 when set screw 150 is not tightened. When press fit into body 130, first edge 620 of retainer 140 can operatively engage beveled edge 250 of swivel 100 thereby preventing swivel 100 from being removed complete from bore 500 of body 130. Retainer 140 can be used to prevent the various pieces of clamp 10 from coming apart during use and possibly being lost in a patient. However, swivel 100 preferably has enough play that swivel 100 along with rod disc 110 can rotate relative to locking plate 120 and body 130. Alternatively, retainer 140 can be connected to body 130 in various ways, such as welding, adhesives, along with other conventionally available connection methods.

Set screw 150 can include top 700, angled tip 715, threads 720, and star socket 710. Set screw 150 can be threaded into tapped bore 510 of body 130. Other means of tightening set screw 150 besides star socket 710 can be used, such as a phillips head; flat head; bolt head, allen wrench head.

Screw 20 can include shank 30 and course threaded portion 40. For tightening screw 20 can also include star socket 70. Other means of tightening screw 20 besides star socket 70 can be used, such as a phillips head; flat head; bolt head, allen wrench head.

Rod 80 can be a shaft and include a circular cross section.

The locking mechanism of clamp 10 will now be described. Clamp 10 can comprise body 130, locking plate 120, rod disc 110, and swivel 100. Set screw 150 can be used to lock in place swivel 100, rod clamp 110, and locking plate 120. Rod 80 can be connected to body 130 through opening 210 of swivel 100. Bone screw 20 can be connected to body 130 through bore 540. Before set screw 150 is tightened (locking clamp 10) both rod 80 and bone screw 20 can be adjusted in all directions as described in the discussion of FIG. 3. However, after set screw 150 is used to lock clamp 10, both rod 80 and screw 20 will be held firmly in place.

To assemble clamp 10, base 240 of swivel is placed through first bore 320 of rod disc 110, through bore 410 of locking plate 120, and then through bore 500 of body 130. Arm 440 of locking plate 120 enters opening 530 of body 130, thereby preventing relative rotation between body 130 and locking plate 120. Plurality of teeth 420 of locking plate 120 are facing plurality of teeth 350 of rod disc 110, however, when clamp 10 is not locked these two sets of teeth do not engage each other and rod disc 110 can rotate relative to locking plate 120. When locked these two sets of teeth engage each other preventing relative rotation. Part of head 200 of swivel 100 sits in second bore 330 of rod disc 110 and head 200 will rotate with rod disc 110. Recess 310 of rod disc 110 preferably is aligned with opening 210 of swivel 100. Such alignment will allow rod 80 to at least be partially inserted in opening 210 and rest in recess 310. Recess 310 preferably confirms with the shape of rod 80.

Rod 80 can be at least partially inserted into opening 210 of swivel 100. Bone screw can be inserted at least partially into bore 540 of body 130. When clamp 10 is not locked, rod 80 can slide relative to opening 210 (and therefore relative to clamp 10). Also when not locked rod 80 can rotate relative to clamp 10 because swivel 100 and rod disc 110 can rotate relative to body 130. When not locked screw 20 can slide relative to body 130 (and therefore relative to clamp 10). Also when not locked screw 20 can rotate inside of bore 540 of body 130.

To lock clamp 10, set screw 150 can be threaded into tapped bore 510. Tip 715 of set screw 150 will contact base 240 of swivel 100 causing swivel 100 to be pulled further into bore 500 of body 130. Pulling swivel 100 into body 130 causes plurality of teeth 420 of locking plate 120 to engage plurality of teeth 350 of rod disc 110 thereby preventing relative rotation between rod disc 110 and locking plate 120. Because locking plate 120 is restricted from rotating relative to body 130 (via arm 440 of locking plate 120 being at least partially inserted in opening 530 of body 130) rod disc 110 will also be restricted from so rotating. Head 200 of swivel 100 at least partially seating in second bore 330 of rod disc 110 also prevents relative rotation of swivel 100 in relation to body 130. Swivel 100 being pulled inside of body 130 also causes rod 80 to be frictionally engaged between bore 210 of swivel 100 and recess 310 of rod disc 110. In effect rod 80 is squeezed between rod disc 110 and bore 210. When frictionally engaged rod 80 is restricted from moving relative to body 130 in all manners (e.g., sliding or rotating). Swivel 100 being pulled further into bore 500 of body 130 causes bore 210 to pull on rod 80, rod 80 then pushes on rod disc 110, rod disc 100 then pushes on locking plate 120, arm 440 of locking plate 120 then pushes through opening 530 on screw 20. Screw 20 is thereby frictionally engaged between arm 440 of locking plate 120 and bore 540 of body 130. When frictionally engaged screw 20 is restricted from moving relative to body 130 in all manners (e.g., sliding or rotating). In such manner both rod 80 and screw 20 can be securely held in clamp 10.

A single version clamp 10 has been disclosed. Preferably, both left and right hand versions of clamp 10 will be used on the left and right hand sides of a fusion. Persons of ordinary skill in the art will understand the mechanics of making left and right hand versions of clamp 10. FIGS. 6 and 7 show left and right hand versions of clamps 10. Clamps 10A and 10B are left hand versions and clamps 10C and 10D are right hand versions. Left and right hand versions are used to have a symmetry between positioning of screws 20 and heads 100 of swivels 100. If only a single version of clamp 10 was used the clamps 10 used on the left hand side would appear to be offset from the clamps used on the right hand side. An alternative method of allowing a single clamp 10 to be used as both a left and right hand version is to have tapped bore 510 extend completely through body 130. To switch from the left to right hand version in this alternative embodiment, set screw 150 is switched from entering tapped bore 510 on opposite sides.

The following is a list of reference numerals:

LIST FOR REFERENCE NUMERALS

| (Part No.) | (Description) |
| --- | --- |
| 10 | clamp |
| 20 | screw |
| 24 | driver |
| 26 | arrow |
| 27 | arrow |
| 28 | arrow |
| 30 | shank |
| 32 | ribs |
| 40 | coarse thread |
| 50 | fine thread |
| 60 | mid portion |
| 70 | star socket |
| 80 | rod |
| 100 | swivel |
| 110 | rod disc |
| 120 | locking plate |
| 130 | body |
| 140 | retainer |
| 150 | set screw |
| 200 | head |
| 210 | opening |
| 220 | mid-portion |
| 230 | shaft |
| 240 | base |
| 250 | beveled edge |
| 260 | bottom |
| 270 | face |
| 272 | edge |
| 274 | edge |
| 300 | top |
| 310 | recess |
| 320 | first bore |
| 330 | second bore |
| 340 | bottom |
| 350 | plurality of teeth |

LIST FOR REFERENCE NUMERALS

| (Part No.) | (Description) |
| --- | --- |
| 400 | top |
| 410 | bore |
| 420 | plurality of teeth |
| 430 | edge portion |
| 440 | arm |
| 450 | cup |
| 452 | plurality of ribs |
| 453 | angle |
| 454 | angle |
| 460 | bottom |
| 500 | bore |
| 510 | tapped bore |
| 520 | recessed area |
| 530 | opening |
| 540 | bore |
| 550 | threads |
| 560 | edge |
| 570 | plurality of ribs |
| 580 | angle |
| 590 | bore |
| 600 | top |
| 610 | shaft |
| 620 | first edge |
| 630 | second edge |
| 640 | curved surface |
| 650 | bottom |
| 700 | top |
| 710 | star socket |
| 715 | tip |
| 718 | point |
| 720 | threads |
| 800 | vertebra |
| 810 | vertebra |
| 815 | arrow |
| 820 | arrow |
| 830 | arrow |
| 840 | arrow |
| 850 | arrow |
| 860 | arrow |
| 870 | arrow |
| 880 | arrow |
| 890 | arrow |

All measurements disclosed herein are at standard temperature and pressure, at sea level on Earth, unless indicated otherwise. All materials used or intended to be used in a human being are biocompatible, unless indicated otherwise. The components of the clamp 10 are preferably constructed from titanium grade 6AL-4VELI which is a standard medical grade of titanium. The type and heat treatment of material can be determined by those of ordinary skill in the art based on the stress and forces encountered by the individual components. However, other materials can be used which are compatible with the body. For example surgical steel can be used along with polymers of sufficient strength.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A method for connecting a connection assembly for a spinal implant, comprising the steps of:
   (a) providing first and second connectors, each connector having a longitudinal center line;
   (b) providing a connection assembly, the connection assembly comprising a body, the body including a body opening for receiving at least a portion of a first connector; a swivel having first and second ends and being operatively connected to the body, the first end including a swivel opening for receiving at least a portion of a second connector; a locking plate having an arm at least partially extending into the body opening; a locking unit operatively connected to the body and contacting the second end of the swivel; and whereby activation of the locking unit causes the arm to engage the first connector and swivel opening to lock the second connector thereby preventing relative rotation between the first and second connectors;
   (c) positioning the body opening over a desired portion of the first connector;
   (d) positioning the swivel opening over a desired portion of the second connector, wherein the longitudinal centerline of the first connector is in a skewed position relative to the longitudinal centerline of the second connector; and
   (e) activating the locking unit.

2. The method of claim 1, wherein in step "b" the locking unit comprises a set screw, and the swivel comprises a base, the set screw engaging the base when the locking unit is activated.

3. The method of claim 2, wherein in step "b" the locking unit comprises a retainer, the retainer being in contact with the set screw when the set screw engages the base.

4. The method of claim 1, wherein in step "b" wherein the arm includes a plurality of ridges.

5. The method of claim 4, wherein in step "b" the first connector includes a plurality of ridges which engage the plurality of ridges of the arm.

6. The method of claim 4, wherein in step "b", wherein the body opening include a plurality of ridges which engage the plurality of ridges of the arm.

7. The method of claim 1, wherein in step "b" the connection assembly further comprises a disc operatively connected to the swivel and locking plate, the disc and locking plate each including a plurality of teeth wherein when the locking unit is activated relative rotation is prevented between the locking plate and disc.

8. The method of claim 7, wherein in step "b" the disc includes a recess which engages the swivel and relative rotation between the disc and swivel is prevented.

9. The method of claim 1, wherein in step "b" the first connector is offset from the second connector in at least two cartesian directions.

10. The method of claim 1, wherein in step "e" activation of the locking unit tends to pull the swivel towards the body.

11. The method of claim 1, wherein in step "b" the first connector is a screw and the second connector is a rod.

* * * * *